US006685651B2

(12) United States Patent
Anker et al.

(10) Patent No.: US 6,685,651 B2
(45) **Date of Patent: *Feb. 3, 2004**

(54) PERIODIC BREAST SELF-EXAMINATION PROMPTING DEVICE

(76) Inventors: Denise M Anker, 1066 Indian Hills Dr., Laramie, WY (US) 82072; Marvin L Odefey, 9623 Townsville Cir., Littleton, CO (US) 80130

( * ) Notice: Subject to any disclaimer, the term of this patent is extended or adjusted under 35 U.S.C. 154(b) by 0 days.

This patent is subject to a terminal disclaimer.

(21) Appl. No.: 10/411,820

(22) Filed: Apr. 11, 2003

(65) Prior Publication Data

US 2003/0191375 A1 Oct. 9, 2003

Related U.S. Application Data

(63) Continuation-in-part of application No. 10/132,859, filed on Apr. 24, 2002.

(60) Provisional application No. 60/288,348, filed on May 2, 2001.

(51) Int. Cl.[7] .................................................. A61B 5/00

(52) U.S. Cl. ..................... 600/551; 368/10; 340/309.16

(58) Field of Search ................................. 600/300–301, 600/551, 549, 595; 128/897; 340/309.16, 309.4; 368/10, 12, 107, 109; 315/169.3; 434/416

(56) References Cited

U.S. PATENT DOCUMENTS

| | | | | |
|---|---|---|---|---|
| 5,207,582 A | | 5/1993 | Michelson | |
| 5,293,098 A | * | 3/1994 | Brownell | 315/169.3 |
| 5,474,064 A | | 12/1995 | Rohrberg | |
| 5,494,442 A | | 2/1996 | Hecht | |
| 5,524,101 A | * | 6/1996 | Thorgersen et al. | 368/10 |
| D377,832 S | | 2/1997 | Jacober | |
| 5,657,753 A | | 8/1997 | Jacober | |
| 6,575,903 B1 | * | 6/2003 | Collins | 600/300 |

* cited by examiner

*Primary Examiner*—Max F. Hindenburg
*Assistant Examiner*—Michael Astorino
(74) *Attorney, Agent, or Firm*—Leyendecker Law Offices; Kurt Leyendecker

(57) ABSTRACT

A prompting device that can be utilized to remind a user to periodically and regularly perform a breast self-examination is described. The device includes a controller to measure a predetermined interval of time. A proximity sensor is provided to detect a person within proximity of the device after the predetermined time interval has expired. If a person is detected, the controller triggers an alarm alerting the person to perform a task such as examining her breasts. If someone other than the intended user activates the proximity sensor, a means for indicating the person is not the intended user is provided so that the alarm can be disenabled for a delay time period before being re-enabled to subsequently notify the intended user. In at least one operational mode of the device, the predetermined time interval is measured cyclically so that the user is periodically reminded to perform the breast self-examination.

22 Claims, 4 Drawing Sheets

PERIODIC BREAST SELF-EXAMINATION PROMPTING DEVICE

RELATED APPLICATIONS

This application is a continuation-in-part (CIP) of U.S. patent application Ser. No. 10/132,859, entitled Breast Self Examination Prompter Device, filed on Apr. 24, 2002, which is still pending. Application Ser. No. 10/132,859 claimed the benefit of a similarly entitled Provisional Application Ser. No. 60/288,348 filed on May 2, 2001. Both related applications are incorporated herein in their entirety.

FIELD OF THE INVENTION

This invention relates to a timing and prompting device. More particularly, this invention relates to a device that alerts and prompts a user within its proximity that a period of time has passed to remind the user to perform a task, such as a breast self-examination.

BACKGROUND OF THE INVENTION

Breast cancer is the most common cancer among women, other than skin cancer. It is the second leading cause of cancer death in women, after lung cancer. The American Cancer Society predicts there are several hundred thousand new cases of breast cancer each year with some forty thousand deaths resulting from the disease. Breast cancer also occurs in men, although much less often.

The earlier breast cancer is found, the better the chances for successful treatment. Because early breast cancer does not produce symptoms, it's important for all women to follow the guidelines of the American Cancer Society for finding breast cancer early. These include the following:

1. A mammogram and a breast exam by a doctor or nurse (clinical breast examination) every year for women over the age of 40.
2. Between the ages of 20 and 39, women should have a clinical breast exam every 3 years.
3. All women over 20 should do breast self-examination (BSE) every month. Together, these methods offer the best chance of finding breast cancer early.

With the above in mind, when is the best time for a woman to do a breast self-examination? This is all dependent upon a woman's menstrual cycle. The average woman's cycle is 28 days. Day one of a woman's menstrual cycle is the first day of menstrual bleeding. The end of the cycle is the first day prior to the beginning of the subsequent menstrual cycle. It is recommended by the medical community that a woman conduct a breast self-examination about one week after the start of the menstrual cycle or in other words days 6–14. A woman's hormone levels are lower at this time causing the woman's breasts to be less tender and less swollen. Accordingly, a woman will experience less discomfort when performing the self-examination during this time, and because of the reduced discomfort, a woman is more likely to perform a more thorough and complete exam on herself.

All menstrual cycles are not created equal. Women and their menstrual cycles or lack of menstrual cycles are categorized as provided below:

1. Women with "regular" or predictable menstrual cycles.
2. Women with "irregular" or unpredictable menstrual cycles. These women having sometimes no idea when the start of their next menstrual cycle might be.
3. Women using birth control pills or birth control patches. These women have menstrual cycles that are dictated by the hormones in the pills or patches. Typically, these women experience regular menstrual cycles that are 28 days in length.
4. Women that have no menstrual cycle. There are a variety of reasons why a woman will not have a menstrual cycle including, but not necessarily limited to, (i) having had a hysterectomy, (ii) having gone through menopause, (iii) participating in a hormone therapy, (iv) being pregnant, and (v) participating in vigorous or excessive exercise.

It is easy for a woman to forget to do her breast self-examination every month due to the everyday pressures of life. The prior art describes several products that can assist a woman in remembering to perform her examination. For instance, U.S. Pat. No. 5,207,582 provides a waterproof tablet along with a grease pencil to record the results of a breast self-examination. Many health care professionals suggest that the breast self-examination be performed when the breasts are wet, such as when taking a shower or bath, because the water helps lubricate the skin and makes the examination easier to perform. Accordingly, the waterproof tablet can be used in a shower or bath. In addition to permitting the user to record examination results, the tablet includes a calendar to record the dates of her past examinations and serves as a visual reminder concerning when she should perform her next examination. Such a device is only useful if the woman can determine her next exam date on the provided calendar and is further prompted to perform the breast self-examination. Given the everyday stress and rigors of a busy lifestyle especially early in the morning when a woman typically bathes or showers, a woman may procrastinate and fail to record the necessary information, thereby defeating the purpose of the calendar included on the tablet. Subsequently, she may miss her opportunity to perform her breast self-examination.

U.S. Pat. No. 5,494,442 describes a device conceptually similar to the above tablet comprising a plurality of transparent overlays that a woman uses to record the location of any masses found in either of her breasts. Each overlay is placed against and attached to a writing board surface that is designed to be coupled to a shower door or wall. Spaces are provided to write down the dates of the woman's menstrual cycle, as well as, the dates on which she performed a self-examination. Accordingly, the woman is provided with a visual reminder as to when to perform her next examination.

An electronic breast examination reminder device that displays a prompt after the passing of a predetermined time interval that can be utilized to remind a woman to perform a self-examination is described in U.S. Pat. No. 5,657,753 and Des, 377,832 to Jacober et al. The device is water resistant for use in a shower or a bath. Once the time interval has passed, a light begins to flash for up to 24 hours after which time it ceases to flash and the term "Exam" on a provided display flashes until the user indicates she has received the prompt to perform a breast self-examination. If the device is reset or deactivated by someone other than the intended woman, the intended woman may never be reminded to perform a breast examination. Accordingly, the type of prompt used by the device is rather benign comprising a small flashing LED and the term, "Exam" displayed on the device's LCD. This device requires less attention from a woman than the tablet type reminder devices described above as the woman only has to press a button to start the device at the beginning of her menstrual cycle, or after her last examination, and then press a second button to indicate to the device the breast examination has been performed.

The one significant problem with this device is an intended user could conceivably miss the small light when it comes on because there is no audible alarm to catch the user's attention.

SUMMARY OF THE INVENTION

In one preferred embodiment, a breast self-examination prompting device adapted to remind a user to perform a breast self-examination on a regular basis includes a housing and an electrical circuit at least partially contained within the housing. The electrical circuit comprises a proximity sensor adapted to detect the presence of a person such as the user within proximity of the device, an alarm, a controller, and first, second and third switches. The controller is adapted to measure first, second and third time intervals, control the operation of the device, and activate the alarm. Typically, the alarm is activated when both (i) the first time interval has expired and (ii) the presence of a person is detected by the proximity sensor within the second time interval. The controller begins to measure the second time interval after the first time interval has expired and the second time interval is shorter than the first time interval. The first switch is electrically coupled with the controller and is adapted to cause the controller to start the measuring of the first time interval. The second switch is also electrically coupled with the controller and is adapted to cause the controller to either or both (a) deactivate and disenable one or both the alarm and the proximity sensor; and (b) deactivate the device. Finally, the third switch is electrically coupled with the controller and is adapted to cause the controller to (a) deactivate the alarm and (b) temporarily disenable at least one of the alarm and the proximity sensor for the third time interval. The third time interval is shorter than the second time interval. If the third time interval expires before the expiration of the second time interval, one or both of the alarm and proximity sensor are re-enabled by the controller.

In another preferred embodiment, a prompting device for reminding a user to perform a task includes a detection means, a prompting means, and a first control means. The detection means is provided to sense a person within proximity of the device. The prompting means is provided to alert the person. The first timer means is provided to measure a first interval of time, and the first control means is provided to activate the prompting means after the first time interval has passed and the person is sensed within proximity of the device.

In another preferred embodiment, a prompting device includes a proximity sensor, an alarm, and a controller. The controller includes clock circuitry and control logic, and the controller is adapted to (i) measure a first interval of time, and (ii) activate the alarm if the presence of a person is detected by the proximity sensor after the first time interval has expired.

In yet another preferred embodiment, a method of operation of a prompting device comprises measuring a first time interval, sensing a person within proximity of the device, and activating an alarm after the first time interval has passed and the person is sensed within proximity of the device.

Numerous other embodiments and variations of the preferred embodiments are also contemplated as is provided in this specification including the appended claims and as would be obvious to one of ordinary skill in the art with the benefit of this disclosure.

BRIEF DESCRIPTION OF THE DRAWINGS

The following figures are provided by way of example and not limitation.

DETAILED DESCRIPTION

Overview

Figure 1:
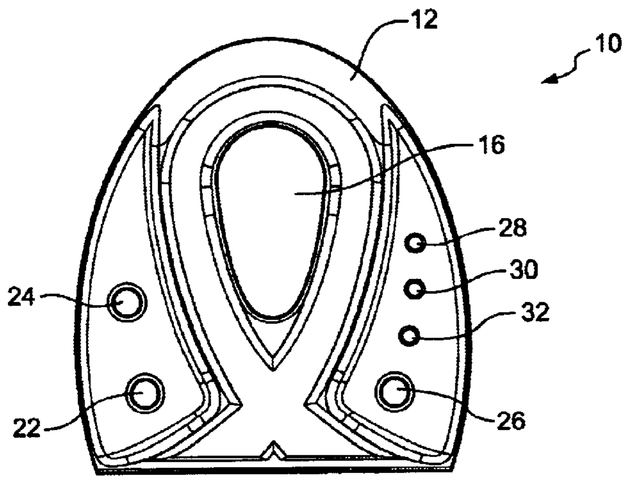
FIG. 1 is a front view of a prompting device enclosed in a water resistant housing according to one preferred embodiment of the invention.

A device for prompting a user after an interval of time has passed is described. The device is primarily described herein in relation to use of the device to remind a woman (or man) to perform a breast self-examination, although other uses of the device are contemplated as well.

In a preferred embodiment, the device comprises an electrical circuit contained within a suitable housing that includes input means such as one or more buttons or switches, a controller typically in the form of a microprocessor for controlling the operation and timing functions of the device, and a proximity sensor.

The device operates in such a manner that the device's alarm or prompt is triggered (or activated) only after both the expiration of a prompting time interval and the detection of a person within the proximity of the device by the proximity sensor. Further, through the input means, a person who is not the intended user of the device can temporarily disenable one of the alarm and the proximity sensor (or detector) without resetting or deactivating the device. The device automatically re-enables (or rearms) the alarm and/or the proximity sensor after a predetermined delay period of time has passed. Accordingly, when the intended user enters within the proximity of the device after the unintended person, the alarm will be triggered again to remind the intended user to perform a certain task such as performing a breast self-examination. This is a significant improvement over the prior art.

Definitions

For purposes of clarity and to avoid confusion, the following definitions are provided herein and are to be applied to the relevant terms throughout this specification.

Enable—to make ready, prepare for use. As used concerning the device's alarm, the term refers to making the alarm and it associated circuitry ready to be activated once the proximity sensor detects a person. Conversely, when the alarm is "disenabled", the alarm will not activate or sound (when a buzzer or other noise maker is utilized) even if the proximity sensor detects the presence of a person. As used herein concerning the proximity sensor, the term refers to readying the sensor and its associated circuitry so that it continuously or intermittently detects for the presence of a person. Conversely, when the proximity sensor is "disenabled", it will not detect for the presence of a person whether continuously or intermittently. Depending on the configuration of the device, readying, enabling and/or disenabling the sensor and/or alarm may simply pertain to various states of the controller especially, although not limited to, when the controller comprises a programmed microprocessor.

Activate—to make active or to turn on. As used herein concerning the alarm of the preferred embodiments and their associated circuitry, the term refers to sounding the alarm when a buzzer or other noisemaker is utilized, or illuminating and/or flashing an LED or light when a visual alarm is utilized. Conversely, to "deactivate" the alarm refers to turning off the noisemaker and/or the illuminated/flashing LEDs or lights. Concerning the proximity sensor, the term refers to sending current through the device to actively detect for a person, such as will occur every eight seconds in one preferred embodiment of the device. Concerning the prompting device itself, the term refers to turning the device on, while "deactivate" refers to turning the device off.

Proximity—the state of being close or near. As used herein, the distance wherein the user is within "proximity" of the device depends on the use of the device. In certain applications, a person may be in "proximity" even if he/she is many feet or yards away from the device. Concerning a breast self-examination prompting device, a person would be within proximity of the device within a distance of about 6–8 feet, more preferably within about 3–6 feet or less and most preferably within about 3 feet or less.

Successive and Iteration—these terms as used herein refer primarily to the ability of the controller and/or its clock circuitry to cyclically and repeatedly measure a selected interval of time in certain operational modes. For instance, when one preferred embodiment breast self-examination device is in a mode that measures either a 28 or 30-day interval, at the expiration or passing of the 28 or 30-day interval, the device will immediately begin to measure a new 28 or 30-day interval. After each measured prompting time interval expires, the alarm and/or proximity sensor are enabled to alert a person who comes within proximity of the device.

A Breast Self Examination Prompting Device

One preferred embodiment of the interval-prompting device 10 for use to remind a user to perform a breast self-examination is illustrated in FIGS. 1–4. It is appreciated that variations and alternative embodiments of the device may be used to remind a person to perform any task on a periodic basis as is discussed in greater detail in the "Alternative Embodiments" subsection below.

Referring to FIG. 1, the device typically comprises (i) a water-resistant housing 12 comprised of a plastic material suitable for use in a shower or in other locations where the device may be exposed to water, and (ii) an electrical circuit (see FIGS. 2–4) substantially enclosed within the housing. In variations of the preferred embodiment, the housing can be comprised of other materials. Further, if the device is to be used in a location other than where it might be routinely exposed to water, the housing need not be water resistant or waterproof. The housing can also include an opening (not shown) typically molded into the topside for receiving a rope, cord or chain (not shown) therethrough for use in hanging the device such as from a showerhead. The configuration of the device and its housing as illustrated in FIG. 1 is merely exemplary. Many variations of the housing are contemplated as would be obvious to one of ordinary skill in the art with the benefit of this disclosure.

Input means in the form of several buttons 22, 24 and 26 are provided on the front side of the device to permit the user to interface with the device. A "Start" button 26 is provided for turning the device on and off. An "Exam Complete" button 22 is provided for signaling the electronic circuitry that the intended user has received the prompt to perform a breast self-examination. A "Not Me" button 24 is provided to (i) permit a person other than the intended user to turn off and/or deactivate the alarm or prompting function of the device for an interval of time referred to herein as the alarm delay time period, and (ii) permit the user to select a prompting time interval. Although buttons are shown in the illustrated preferred embodiment any number of suitable input means can be utilized to interface with the device such as, but not limited to dials, rocker switches, toggle switches, touch sensitive switches, slide switches, and any other type of switch. Further, the number of input means can vary, as well as, their configuration and placement on the housing of the device. Further, the specific designations of the various buttons, switches or other input means can vary as well.

Three LEDs 28, 30 and 32 (or lights) are provided on the front side of the device to indicate the operating mode of the device to the user. The operational modes of the device correspond to the prompting time interval chosen after the device is activated. When a 7-day prompting time interval is chosen, the topmost LED 28 is illuminated to indicate the device is in the first mode. When a 28-day prompting time interval is chosen, the middle LED 30 is illuminated to indicate the device is in a second mode. Finally, when a 30 day prompting time interval is chosen, the bottom LED 32 is illuminated to indicate the device is in a third mode. In variations of the preferred breast self-examination prompting device, the LEDs can be replaced with any suitable indicator means such as, but not limited to lights, an alphanumeric display panel (typically comprising a plurality of arranged LEDs or LCDs), and indications imprinted on the housing of the device to correspond to a selectable position of a mode selection dial or switch.

The first mode is typically for use by women that have regular menstrual cycles and do not utilize oral contraceptives or a contraceptive patch. Additionally, the first mode is the preferred mode for use by women with irregular menstrual cycles. To select the first mode, a female user first turns the device on by depressing the "Start" button 26 and then the user depresses the "Start" button a second time to begin measuring the 7-day prompting time interval. The 7-day LED 28 will flash once every two minutes to indicate the device is operating properly and is in the first mode. Preferably, the user starts the first mode at the start of the user's menstrual cycle (i.e. when menstrual flow begins) so that the device's alarm is triggered when the user moves into the device's proximity after the seventh day of the user's cycle reminding the user to perform a breast self-examination at the optimum point in her menstrual cycle. It is to be appreciated that the actual prompting time interval can vary somewhat. For instance, in a variation of the preferred embodiment, the time interval of the first mode can be anywhere from days 6–14, although a 7-day time interval is the first day of this preferable time period.

The second mode is typically for use by women using oral contraceptives or a contraceptive patch that cause them to have very regular 28-day menstrual cycles. To select the second mode, a female user (i) turns the device on by depressing the "Start" button 26, (ii) depresses the "Not Me" button to select the second mode and illuminate the 28-day LED 30, and (iii) depresses the "Start" button again to begin measuring the 28-day prompting time interval. The 28-day LED 30 will flash once every two minutes to indicate the device is operating properly and is in the second mode. Preferably, the user should start the device for the first time on day one of her oral contraceptive cycle or on same day as she applies her first patch. Hormones in the oral contraceptives and transdermal patches fluctuate and are designed to fall around the 21rst day, causing a woman to experience her menstrual cycle. Approximately one week later, about the $28^{th}$ day, the device will activate the alarm to prompt the user to perform her beast self-examination. In the second mode, the device will automatically begin measuring a new 28-day time interval in a cyclical manner once a previous prompting time interval has been measured. Accordingly, a women using this mode only has to start the device once and it will continuously remind her to perform her breast self-examination on the seventh day of her menstrual cycle for an indefinite period or until the battery dies. It is to be appreciated that the prompting time interval of the second mode can be other than 28 days. For example, if a contraceptive patch or pill is introduced that causes a women to have a 26, 27 or 29 day cycle instead of a 28-day cycle, a variation of the device can be provided that has a mode that measures a suitable time interval.

The third mode is typically for use by women that do not have menstrual cycles. Additionally, men can also utilize this mode. To select the third mode, a user (i) turns the device on by depressing the "Start" button 26, (ii) depresses the "Not Me" button twice to select the third mode and illuminate the 30-day LED 32, and (iii) depresses the "Start" button again to begin measuring the 30-day prompting time interval. The 30-day LED 32 will flash once every two minutes to indicate the device is operating properly and is in the third mode. In the third mode, the device will automatically begin measuring a new 30-day time interval in a cyclical manner once a previous prompting time interval has been measured. Accordingly, a person using this mode only has to start the device once and it will continuously remind her/him to perform her/his breast self-examination every 30 days for an indefinite period or until the battery dies.

Referring back to FIG. 1, a center panel 16 is provided that is transparent to infrared or other applicable wavelengths. A proximity sensor 34 (as described below in reference to FIGS. 2–4) is provided behind the center panel. When an alarm of the device is enabled after the prompting time interval of anyone of the three described modes has passed, the proximity sensor periodically checks for the presence of a person within its proximity. If a person is detected, the alarm activates to remind the person to perform the breast self-examination. It is to be appreciated any suitable type of proximity sensor or detection means may be utilized to detect the presence of a person such as, but not limited to, a motion sensor, a pyro-electric sensor, and an infrared thermopile sensor. In one preferred embodiment, an infrared thermopile sensor assembly that is sensitive to infrared radiation having wavelengths of about 7–13 microns is utilized. Humans typically emit infrared radiation in the 7–13 micron wavelength spectrum. It is appreciated that the composition and transparency of the center panel can vary depending on the particular type of proximity sensor utilized and the operational wavelength associated with the sensor.

Figure 2:
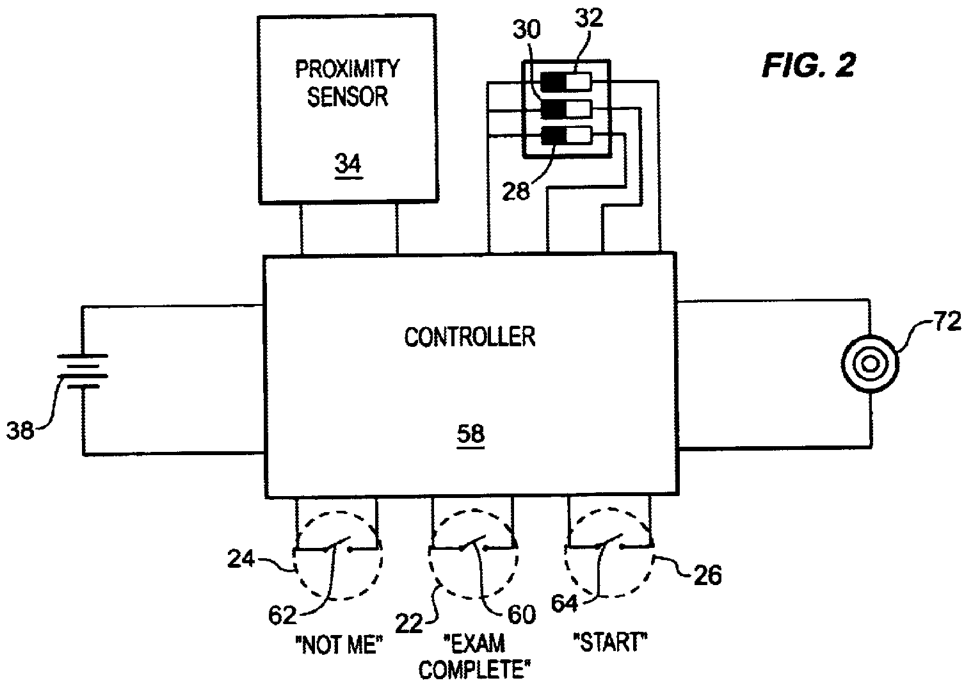
FIG. 2 is a generalized and simplified schematic of the electrical circuit utilized in one preferred embodiment of the device.
Figure 3:
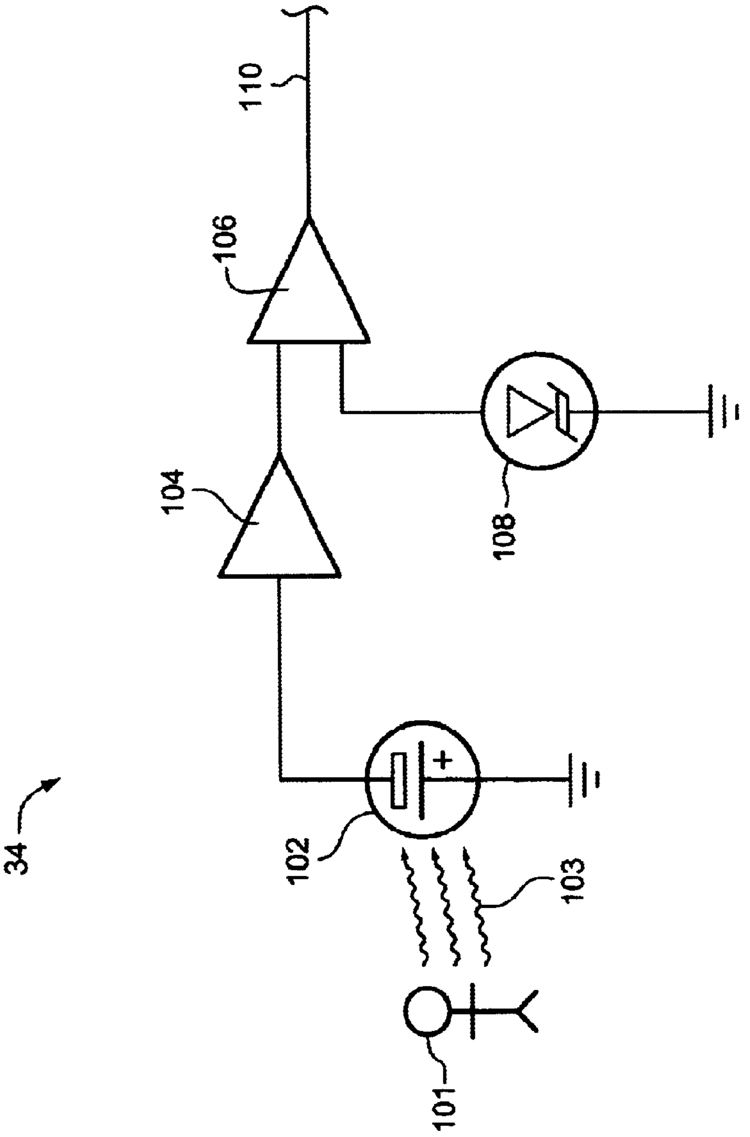
FIG. 3 is a simplified and generalized schematic of one type of proximity sensor utilized in one preferred embodiment of the device.
Figure 4:
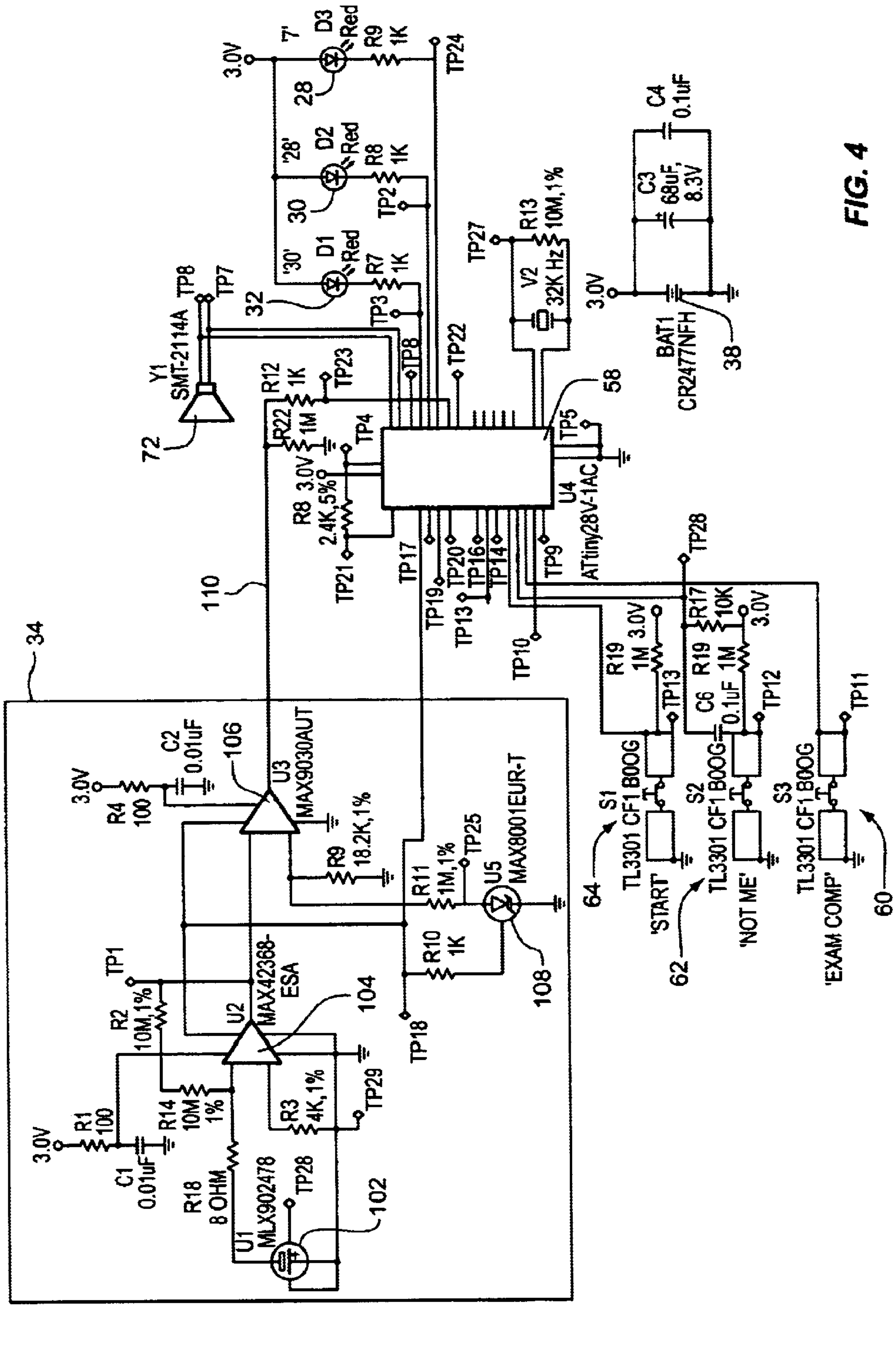
FIG. 4 is a detailed schematic of the electrical circuit utilized in one preferred embodiment of the device.

Referring to FIGS. 2–4, the electrical circuit of one preferred embodiment is illustrated.

FIG. 2 is a generalized and simplified schematic of the electrical circuit utilized in one preferred embodiment of the device. The electrical circuit of one preferred embodiment of the device includes: the proximity sensor 34; a plurality of switches 60, 62 and 64 corresponding to the "Exam Complete" button 22, the "Not Me" button 24 and the "Start" button 26 respectively; an alarm 72; 7-day, 28-day and 30-day indicator LEDs 28, 30 and 32; and a controller 58 for coordinating the operation of the device and measuring the relevant time intervals to which all the other components are electrically connected. For clarity, some of the electrical connections and circuitry have been omitted from this illustration. For instance, the direct connection of the proximity sensor 34 with the battery 38 is not shown.

The controller 58 typically comprises a specially programmed microprocessor but in alternative embodiments of the electrical circuit, a control means comprising hard-wired circuitry can be utilized. Further, rather than comprising a single integrated circuit, a controller (or control means) comprising a plurality of integrated circuits or a collection of transistors and other basic components can be utilized. The controller includes: (i) a timer means such as clock or timer circuitry for measuring time; (ii) various input and output connections with the switches 60, 62 and 64, the proximity sensor 34, the indicator LEDs 28, 30 and 32, and the alarm 72; and (iii) control logic to coordinate the operation of the device relative to input from a user and relative to timing concerning specific time intervals and time periods being measured by the clock circuitry. As can be appreciated in variations and alternative embodiments, the control logic and the clock circuitry can comprise separate chips wherein the clock circuitry sends a signal to the control logic when a relevant time interval or period has begun or expired. The operation of the controller of one preferred embodiment is discussed in greater detail in the "Operation of the Breast Self-Examination Prompting Device" subsection below.

In one preferred embodiment the proximity sensor 34 comprises an infrared thermopile assembly that measures infrared heat energy of a specific wavelength emitted by humans. The thermopile assembly is enabled after the expiration of the relevant prompting time interval and activates intermittently thereafter to sense for a person. The thermopile of one preferred embodiment is activated every eight seconds, although other time spans between activations can be used. Further, in variations and alternative embodiments, the thermopile or other proximity sensor can be continuously active during a time period following the expiration of the relevant prompting time interval. The basic operation of the thermopile assembly can be better understood with reference to FIG. 3. When a person 101 passes within the proximity of the device, infrared energy 103 from the person impinges on a thermoelectric pile 102. The thermoelectric pile converts the infrared energy incident on it into a small amount of electrical energy that is transmitted to an amplifier 104. The amplifier amplifies the magnitude of the voltage from the electrical energy and sends it to a threshold comparator 106. The threshold comparator compares the amplified voltage to a reference voltage that is provided by a reference voltage generator 108. If the amplified voltage is greater than the reference voltage, a signal is sent to the controller over line 110 indicating that a person has been detected. It is appreciated that the diagram of FIG. 3 is simplified for clarity and that other components are included in the actual thermopile assembly of one preferred embodiment. For instance, several capacitors and resistors are included in the actual assembly along with electrical traces that are coupled with the battery 38 of the electrical circuit. Additionally, another electrical trace that sends an electrical signal from the controller to the assembly on an intermittent basis (every 8 seconds in one preferred embodiment) to activate the thermopile assembly is also not illustrated in FIG. 3. A more detailed schematic of the thermopile assembly is provided in FIG. 4.

Referring back to FIG. 2, the battery 38 utilized in one preferred embodiment is a three-volt lithium cell that is permanently sealed in the housing 12. This battery provides the device with about an eight to ten year operating lifespan under normal operating conditions. In variations and alternative embodiments, a user-replaceable cell can be utilized. In another alternative embodiment, an AC adapter can be provided such that the device can be powered by one or both AC and DC power.

The alarm 72, or prompting means, typically comprises a buzzer, a speaker or some other type of noisemaking device. Further, the alarm can be visual such as flashing lights or LEDs. In one preferred embodiment the applicable indicator LED 28, 30 or 32 blinks when the alarm has been activated. Accordingly, the alarm can comprise both visual and auditory prompters.

FIG. 4 is a detailed schematic of the electrical circuit of one preferred embodiment. As applicable the various components discussed and described above with reference to FIGS. 2 and 3 are labeled with similar reference numbers in this Figure.

It is to be appreciated that FIGS. 2–4 represent an exemplary electrical circuit that can be utilized in a preferred embodiment of the prompting device. Many different configurations of the electrical circuit that can provide similar functionality as the circuit described and illustrated herein are possible and are considered within the scope of the present invention. For example, instead of using the clock circuitry of the controller to intermittently power-up the proximity sensor 34, this function can be handled by an RC circuit 44 as described in the parent application No. 10/132,859, which has been incorporated by reference. Further, although the indicator LEDs 28, 30 and 32 of the illustrated preferred embodiment are made to flash in a certain pattern for a certain time interval when the alarm is activated, a separate light, LED or a kinetic object (such as a rotating disk with contrasting painted portions) can be provided as a visual alarm in alternative embodiments.

Operation of the Breast Self Examination Prompting Device

Figure 5:
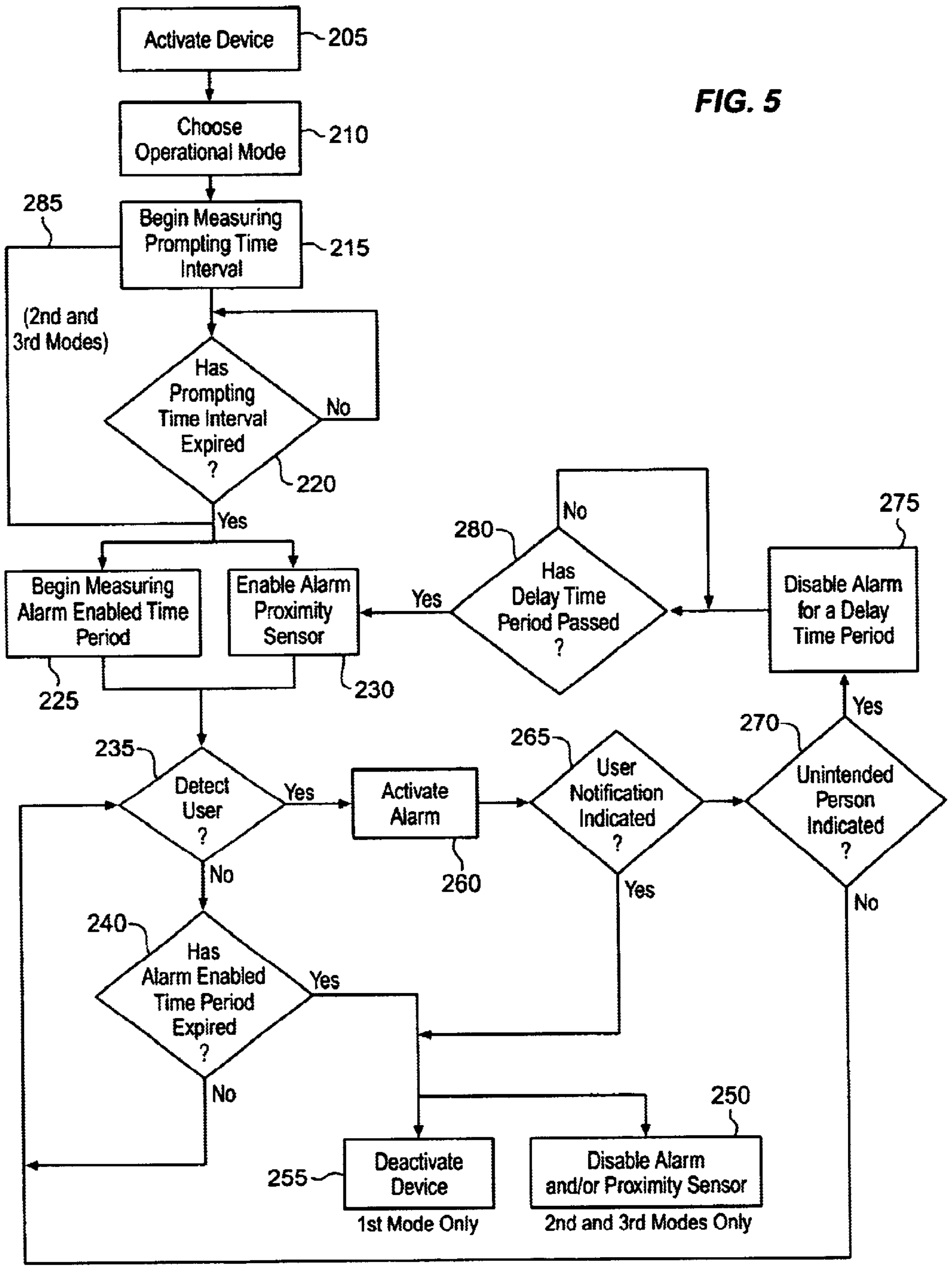
FIG. 5 is a flow chart illustrating the operation of one preferred embodiment of the device.

FIG. 5 is a flow chart outlining the operation of one preferred embodiment breast self-examination prompting device.

When using the device for the first time or after the device 10 has been inactivated, a user first depresses the "Start" button 26 to power-up the device as indicated in block 205.

Next, as indicated in block 210, the user chooses the desired operational mode with its associated prompting time interval. As discussed above, women with irregular or regular menstrual cycles that are not on oral contraceptives or the contraceptive patch would typically be advised to choose the first mode with a 7-day measured time interval. Women using oral contraceptives or the contraceptive patch would be advised to choose the second mode with a 28-day measured time interval, and women and men that do not have menstrual cycles would be advised to choose the third mode with a 30-day measured time interval. In one preferred embodiment, the first mode is the device's default mode and is automatically selected when the device is activated as is indicated by the illumination of the associated 7-day indicator LED 28. The second mode is chosen by depressing the "Not Me" button once, which also causes the 7-day indicator LED to turn off and the 28-day indicator LED 30 to illuminate. The third mode is chosen by depressing the "Not Me" button twice, which causes the 7-day indicator LED to turn off and the 30-day indicator LED 32 to illuminate.

After choosing an operational mode, the user depresses the "Start" button for a second time to cause the controller 58 and its associated clock circuitry to begin measuring the specified prompting time interval as indicated in block 215. While the prompting time interval is being measured, the proximity sensor and the alarms are typically disenabled.

As indicated in decision block 220, the controller 58 will determine if the prompting time interval has passed. If the time interval has not passed, the controller will do nothing as its clock circuitry continues to measure the prompting time interval. Once the interval has passed, however, the controller will enable the alarm 72 and the proximity sensor 34 as indicated by block 230 so that any person within the proximity of the device when the proximity sensor is intermittently activated will cause the alarm to be activated. Additionally, the controller will begin to measure an alarm-enabled time period as indicated by block 225. The alarm-enabled time period is the amount of time after the selected prompting time interval has passed that the proximity sensor and the alarm will remain enabled. In one preferred embodiment, the alarm-enabled time period is set at 5 days, although variations of the device can be configured for other suitable time periods.

Additionally when the device is in the second and third modes with their respective 28 and 30-day time intervals, the controller will automatically begin to measure the selected prompting time interval again as indicated by line 285. Accordingly, in either the second or third modes, the controller will simultaneously measure the alarm-enabled time period and a new prompting time interval after the preceding prompting time interval has expired.

Referring to decision block 235, the proximity sensor 34 will intermittently check for the presence of a person during the alarm-enabled time period. If a person is detected, the proximity sensor will signal the controller 58, which will in turn activate the alarm 72 as indicated by block 260. The alarm typically comprises a buzzer (or other noisemaker), although variations of the device may include other types of alarms and combinations of alarms. In one preferred embodiment, the indicator LED corresponding to the selected prompting time interval will also double flash in succession when the alarm is activated.

Referring to blocks 240 and 250, if (i) the intended user is not detected during the alarm-enabled time period, (ii) the alarm-enabled time period expires, and (iii) the device is operating in the second or third modes, the proximity sensor 34 and the alarm 72 will be disenabled. The alarm and proximity sensor will not be re-enabled until the next iteration of the prompting time interval (28 or 30-days), which is being concurrently measured, has passed.

Referring to blocks 240 and 255, if (i) the intended user is not detected during the alarm-enabled time period, (ii) the alarm-enabled time period expires, and (iii) the device is operating in the first mode, the device will deactivate or turn-off. After the device as deactivated, a user must re-activate the device and select a new prompting time interval to use the device.

Referring back to block 260, the alarm buzzer 72 will continue to sound and the appropriate LED will continue to flash as long as a person is detected to be within the proximity of the device. In one preferred embodiment, the alarm buzzer sounds intermittently every eight seconds and the LED flashes in unison with the audible alarm, wherein the eight second interval corresponds to the proximity sensor being activated to detect for the presence of a person. In one preferred embodiment, if the person leaves the proximity of the device, the alarm will deactivate. In other embodiments and variations, the alarm may continue to sound after it is activated until the appropriate user input is provided. Since one preferred embodiment of the device is typically utilized in a bath or shower, the person causing the alarm to activate will typically have just begun washing and leaving the proximity of the device will not be desirable. Accordingly, the user has the option of depressing either the "Exam Complete" button 22 or the "Not Me" button 24 to turn-off or temporarily disenable the alarm respectively.

If the intended user is the person who sets off the alarm, she will presumably depress the "Exam Complete" button 22 indicating that she is the intended user and has received notice that she should perform a breast self-examination. See block 265. Presumably, the intended user will then perform the examination before leaving the shower or the bath. Once the button is pushed the device will deactivate as indicated by block 255 if the device is in the first mode, or if the device is in either the second or third modes, the device will deactivate the alarm and disenable the alarm and/or the proximity sensor as indicated by block 250. It is to be appreciated that in the second or third mode, the device will re-enable the alarm 72 and/or proximity sensor 34 when the next iteration of the concurrently measured 28 or 30-day time interval expires.

If a person other than the intended user is the one who sets off the alarm 72, such as the intended user's spouse, he will presumably want to deactivate the alarm so that he may continue his shower or bath in peace without constant prompting from the device. Accordingly, referring to block 270, he would indicate he is not the intended user by depressing the "Not Me" button 24. This action causes the controller 58 to deactivate the alarm, as well as, disenable the proximity sensor 34 and the alarm for an alarm delay time period as indicated by block 275. It is to be appreciated that depressing the "Not Me" button does not effect the clock circuit functions of measuring either or both the prompting time interval and the alarm-enabled time period. In one preferred embodiment, a delay time period of 15 minutes is utilized to permit the person to finish his shower or bath and leave the proximity of the device before the delay time period has passed. Variations of the device can be configured for any suitable delay time period. Referring to block 280 and 230, once the delay time has passed the alarm and the proximity sensor are re-enabled so that the alarm will sound when the next person, such as the intended user, comes within the proximity of the device.

Alternative Embodiments

The preferred embodiments of the invention relate to a breast self-examination device as has been discussed in substantial detail above. The preferred embodiments of the prompting device as illustrated in the accompanying figures and described herein is merely exemplary and is not meant to limit the full scope of the invention. It is to be appreciated that numerous variations to the invention have been contemplated as would be obvious to one of ordinary skill in the art with the benefit of this disclosure. All variations to the invention that read upon the appended claim language are intended and contemplated to be within the scope of the invention.

For instance, an alternative embodiment of the prompting device can be utilized to remind a person or their medical caregiver to administer medication within a certain window of time. Suitable medications can include, but are not limited to, oral medications, subcutaneous and intramuscular injections, intraocular medications and transdermal medications, such as patches. Further, alternative embodiments of the device can be used to remind a person to perform periodic medical or physiological testing or therapy such as, but not limited to blood glucose testing, testicular self-examination, and blood pressure, temperature, pulse, and respiration monitoring. Additionally, the uses of alternative embodiments are not limited to medical or physiological fields. For instance, the device can be utilized to remind a user to pay bills, drink another glass of water, clean a litter box, and any other routine or nonroutine task that can be easily forgotten. Of course, the various time intervals and time periods can be factory set for an alternative embodiment device depending on the intended use of the device. In other variations, however, the various time periods and time intervals can be preset or set by the user to custom tailor the device for a particular use or function.

Variations or substitutions for the various components have been described in the detailed description in regard to preferred embodiments. Many other variations of the components are also possible as would be obvious to one of ordinary skill in the art with the benefit of this disclosure. For instance, in an alternative embodiment device intended for use outdoors or where a sufficient supply of light is available, the device could be powered by a solar cell alone or in combination with a rechargeable battery. Further, depending on the intended use of alternative devices, they can be designed to be placed on or attached to any number different locations near or at an area that a user might frequent including, but not limited to a refrigerator, a vanity mirror, a nightstand, next to a computer and in a vehicle. Variations on the input means can be provided in alternative embodiments such as a computer interface wherein a user can dock the device to a computer to reconfigure the controller and its operation relative to various time intervals and periods and proximity sensor stimuli. For example, in certain applications of an alternative device, it might be desirable to have the device trigger the alarm after the selected prompting time interval has passed only when the proximity sensor detects the presence of a person or some other object for a certain time period or a certain number of times. Further, the indicator LED (or lights) can be replaced with an LCD or LED alphanumeric display that display could provide a running count of the time remaining or the time passed in the prompting time interval currently being measured. Additional alarm mechanisms might be utilized as well. For instance, a lamp could plug into a plug provided in an alternative embodiment of the device with the device causing the lamp to flash when the alarm is activated. Also, an electronic voice can be utilized in place of a buzzer or other noisemaker. In yet another variation, the alarm can send a signal over a wired or wireless telephone or network to, for example, anyone of a phone, a pager, an email account, and a web page. It is also contemplated that an embodiment of the invention can be integrated into another device and provide additional functionality thereto.

We claim:

1. A breast self-examination prompting device adapted to remind a user to perform a breast self-examination on a regular basis, the device comprising:

a housing; and an electrical circuit at least partially within the housing, the electrical circuit including, (1) a proximity sensor adapted to detect the presence of a person, such as the user, within proximity of the device, (2) an alarm, (3) a controller, the controller adapted to (a) measure first, second and third time intervals, (b) control the operation of the device, and (c) initially activate the alarm when only both (i) the first time interval has expired, and (ii) the presence of the person is detected by the proximity sensor within the second time interval, wherein the second time interval is shorter than the first time interval, and the controller is further adapted to begin measuring of the second time interval after the first time interval has expired, (4) a first switch electrically coupled with the controller and adapted to cause the controller to start the measuring of the first time interval, (5) a second switch electrically coupled with the controller and adapted to cause the controller to at least one of (a) deactivate the alarm and disenable one or both the alarm and the proximity sensor, and (b) deactivate the device; and (6) a third switch electrically coupled with the controller and adapted to cause the controller to (a) deactivate the alarm and (b) temporarily disenable at least one of the alarm and the proximity sensor for the third time interval, the third time interval being shorter than the second time interval wherein if the third time interval expires before the expiration of the second time interval, the controller is adapted to re-enable one or both of the alarm and proximity sensor.

2. The device of claim 1, wherein the first, second, and third switches comprise buttons.

3. The device of claim 1, wherein:

the first time interval is one of a set of time intervals including about 7 days, about 28 days, and about 30 days;

the second time interval is about 5 days; and the third time interval is about 15 minutes.

4. The device of claim 1, wherein the alarm comprises one or both of an audible alarm and a visual alarm, the visual alarm including at least one of a light, an LED, an LCD, and a kinetic object.

5. The device of claim 1, wherein at least two of the first, second and third switches comprise the same switch.

6. A prompting device for reminding a user to perform a task, the device comprising:

a detection means for sensing a person within proximity of the device;

an prompting means for alerting the person;

a first timer means for measuring a first interval of time a first control means for initially activating the prompting means only after both the first time interval has passed and the person is sensed within proximity of the device.

7. The prompting device of claim 6 further comprising a second timer means for measuring a second interval of time beginning immediately after the expiration of the first period of time, the second interval of time being shorter than the first interval of time, wherein one, two or all of a group of the detection means, the first control means and the prompting means are enabled only during the second interval of time.

8. The prompting device of claim 7, further comprising a first input means for one or both of (i) deactivating the prompting means, and (ii) deactivating the device.

9. The prompting device of claim 8, further comprising:

a second input means for deactivating the prompting means and for disenabling for a delay period of time one, two or all of a group of (i) the detection means, (ii) the first control means and (iii) the prompting means;

a third timer means for measuring the delay period of time; and a second control means for re-enabling after the delay period of time expires one, two or all of the group of (a) the detection means, (b) the first control means, and (c) the prompting means.

10. The method of claim 9, wherein the first and second control means comprise the same means, and wherein the first, second and third timer means comprise the same means.

11. A method of operation of a prompting device, the method comprising:

measuring a first time interval;

sensing a person within proximity of the device;

initially activating an alarm only after both the first time interval has passed and the person is sensed within proximity of the device.

12. The method of claim 11, further comprising enabling one or both of an alarm and a proximity sensor after the first time interval has expired.

13. The method of claim 11, further comprising measuring a second time interval after the expiration of the first time interval, wherein said activating the alarm occurs only during the second time interval.

14. The method of claim 11, further comprising deactivating the alarm after said activating the alarm in response to a first input.

15. The method of claim 12, further comprising:

(i) deactivating the alarm after said activating the alarm;

(ii) temporarily disenabling one or both of the alarm and the proximity sensor for a delay period of time, both said deactivating the alarm and said temporarily disenabling one or both of the alarm and the proximity sensor being in response to a second input; and (iii) re-enabling one or both of the alarm and the proximity sensor after the delay period has expired.

16. The method of claim 13, further comprising (i) deactivating the alarm after said activating the alarm, (ii) measuring a delay period of time, and (iii) preventing said activating the alarm during the second interval of time until the delay period of time has expired.

17. A prompting device comprising:

a proximity sensor;

an alarm; and a controller including clock circuitry and control logic, the controller being adapted to (i) measure a first interval of time, and (ii) initially activate the alarm only if the presence of a person is detected by the proximity sensor after the first time interval has expired.

18. The prompting device of claim 17, further comprising at least one switch, the controller in response to activation of the at least one switch being further adapted to (a) deactivate the alarm, (b) temporarily disenable one or both of the proximity sensor and the alarm for a delay period of time, (c) re-enable at least one of the alarm and proximity sensor at the expiration of the delay period of time, and (d) re-activate the alarm if the presence of a person is detected by the proximity sensor after at least one of the alarm and proximity sensor is re-enabled.

19. The prompting device of claim 17, wherein the controller is further adapted to (1) measure an alarm-enabled period of time beginning after the first interval of time has expired, and (2) activate the alarm if the presence of a person is detected by the proximity sensor before the expiration of the alarm-enabled period of time.

20. The prompting device of claim 18, wherein the controller is further adapted to (1) measure an alarm-enabled period of time beginning after the first interval of time has expired, and (2) activate the alarm if the presence of a person is detected by the proximity sensor before the expiration of the alarm-enabled period of time.

21. The prompting device of claim 19, wherein the controller is further adapted to successively measure the first interval of time.

22. The prompting device of claim 21, wherein the alarm-enabled period of time is shorter than the first interval of time.

* * * * *